United States Patent [19]
Safar et al.

[11] Patent Number: 5,879,316
[45] Date of Patent: Mar. 9, 1999

[54] PORTABLE AND MODULAR CARDIOPULMONARY BYPASS APPARATUS AND ASSOCIATED AORTIC BALLOON CATHETER AND ASSOCIATED METHOD

[75] Inventors: Peter Safar; S. William Stezoski; Miroslav Klain, all of Pittsburgh, Pa.

[73] Assignee: University of Pittsburgh of the Commonwealth System of Higher Education, Pittsburgh, Pa.

[21] Appl. No.: 835,662

[22] Filed: Apr. 10, 1997

Related U.S. Application Data

[63] Continuation of Ser. No. 637,861, Apr. 25, 1996, Pat. No. 5,820,593, which is a continuation of Ser. No. 396,474, Mar. 2, 1995, abandoned, which is a continuation of Ser. No. 134,769, Oct. 12, 1993, abandoned, which is a division of Ser. No. 637,565, Dec. 28, 1990, Pat. No. 5,308,320.

[51] Int. Cl.$^6$ ................................................. A61M 37/00
[52] U.S. Cl. ................................... 604/4; 604/131; 604/6
[58] Field of Search .......................... 604/4, 5, 6, 131, 604/141

[56] References Cited

U.S. PATENT DOCUMENTS

| | | |
|---|---|---|
| 2,659,368 | 11/1953 | Gibbon, Jr. et al. . |
| 3,211,152 | 10/1965 | Stern . |
| 3,411,506 | 11/1968 | Velasco . |
| 3,506,406 | 4/1970 | Birch, Jr. . |
| 3,516,408 | 6/1970 | Montanti . |
| 3,905,361 | 9/1975 | Hewson et al. . |
| 3,949,734 | 4/1976 | Edwards et al. . |
| 4,116,589 | 9/1978 | Rishton . |
| 4,160,801 | 7/1979 | Badolato et al. . |
| 4,372,914 | 2/1983 | Raible . |
| 4,407,777 | 10/1983 | Wilkinson et al. . |
| 4,540,399 | 9/1985 | Litzie et al. . |
| 4,686,085 | 8/1987 | Osterholm . |
| 4,717,548 | 1/1988 | Lee . |
| 4,741,328 | 5/1988 | Gabbay . |
| 4,756,705 | 7/1988 | Beijbom et al. . |
| 4,796,644 | 1/1989 | Polaschegg . |
| 4,828,543 | 5/1989 | Weiss et al. . |
| 4,861,330 | 8/1989 | Voss . |
| 4,867,738 | 9/1989 | Mintz . |
| 4,894,164 | 1/1990 | Polaschegg . |
| 4,898,168 | 2/1990 | Yule . |
| 4,917,102 | 4/1990 | Miller et al. . |
| 4,932,956 | 6/1990 | Reddy et al. . |
| 5,011,469 | 4/1991 | Buckberg et al. . |
| 5,069,661 | 12/1991 | Trudell . |
| 5,090,958 | 2/1992 | Sahota . |

OTHER PUBLICATIONS

Safar, P. et al., "Cardiopulmonary Bypass For Emergency Resuscitation After Prolonged Cardiac Arrest", *American Journal Of Emergency Medicine*, 2:348 (1984).

(List continued on next page.)

*Primary Examiner*—Corrine M. McDermott
*Assistant Examiner*—Cris L. Rodriguez
*Attorney, Agent, or Firm*—David V. Radack; Arnold B. Silverman; Eckert Seamans Cherin & Mellott, LLC

[57] ABSTRACT

The portable and modular cardiopulmonary bypass apparatus has met the above mentioned needs. The apparatus consists of (i) a first cannula assembly means for withdrawing blood from a patient, (ii) a pump means connected to the first cannula assembly means for receiving the withdrawn blood and for moving the blood through the apparatus, and (iii) a first tubing means connected to the pump means to transport the patient's blood away from the pump means. The apparatus further comprises (iv) oxygenator means for receiving blood from the first tubing means and for oxygenating the blood and (v) second cannula assembly means connected to the oxygenator means for returning the oxygenated blood to the patient. The apparatus is portable so that it can be used by medical personnel anywhere. In addition, the apparatus is adapted to include one or more modules for conditioning the blood, such as modules that include a heat exchanger, blood purifier, plasma and blood cell apheresis device and others. An aortic balloon catheter is also provided.

8 Claims, 5 Drawing Sheets

OTHER PUBLICATIONS

Safar, P. et al., "Resuscitation Of Dogs From Cold–Water Submersion Using Cardiopulmonary Bypass", *Annals Of Emergency Medicine,* 14:5, pp. 25–32 (May 1985).

Safar, P. et al., "Neurologic Outcome After 10 Min Cardiac Arrest Plus 10 Min CPR And Resuscitation With Cardiopulmonary Bypass In Dogs", 17th Annual UAEM Meeting, Philadelphia, May 19–21, 1987, *Annals Of Emergency Medicine,* 16:515 (May 1987).

Safar, P. et al., "Cardiopulmonary Bypass After Prolonged Cardiac Arrest In Dogs", *Annals Of Emergency Medicine,* 16:6 pp. 19–27 (Jun. 1987).

Safar, P. et al., "Cardiopulmonary Bypass After Cardiac Arrest And Prolonged Closed–Chest CPR In Dogs", *Annals Of Emergency Medicine,* pp. 29–36 (Jun. 1987).

Safar, P. et al., "Coronary Perfusion Pressure During External CPR Versus Cardiopulmonary Bypass After Prolonged Cardiac Arrest In Dogs", ACEP 1987 Scientific Assembly, San Francisco, CA, Nov. 2–5, 1987, *Annals Of Emergency Medicine,* 16:1102 (Nov. 1987).

Safar, P. et al., "Improved Neurologic Outcome After Prolonged Cardiac Arrest (CA) In Dogs, Using External CPR (Low Flow) vs. No Flow Prior To Advanced Resuscitation With Cardiopulmonary Bypass (CPB)", SCCM Meeting, Orlando, FL, May 31, 1988, *Critical Care Medicine,* 16:387 (May 1988).

Safar, P. et al., "Reversibility Limits For Heart And Brain Of Ventricular Fibrillation (VF) Cardiac Arrest (CA) In Dogs", SCCM Meeting, Orlando, FL, May 31, 1988, *Critical Care Medicine,* 16:390 (May 1988).

Safar, P. et al., "Emergency Cardiopulmonary Bypass For Resuscitation From Prolonged Cardiac Arrest", *American Journal Of Emergency Medicine,* vol. 8, No. 1, pp. 55–67 (Jan. 1990).

FIG_2

PORTABLE AND MODULAR CARDIOPULMONARY BYPASS APPARATUS AND ASSOCIATED AORTIC BALLOON CATHETER AND ASSOCIATED METHOD

This is a continuation, of application Ser. No. 08/637,861, filed Apr. 25, 1996, U.S. Pat. No. 5,820,593 (which is a Continuation of Ser. No. 08/396,474, filed Mar. 2, 1995 now abandoned which in turn is a Continuation of Ser. No. 08/134,769, filed Oct. 12, 1993 which in turn is a Divisional of Ser. No. 07/637,565, filed Dec. 28, 1990) U.S. Pat No. 5,308,320

BACKGROUND OF THE INVENTION

1. Field Of The Invention

This invention relates to a portable and modular cardiopulmonary bypass apparatus and more particularly it relates to a portable apparatus that can be used to effectively treat patients in suspected terminal states or clinical death. The invention also includes an associated aortic balloon catheter and an associated method.

2. Background Of The Invention

The development of external cardiopulmonary-cerebral resuscitation (CPCR) was initiated by one of the co-inventors herein, Dr. Peter Safar. This breakthrough revolutionized the then embryonic field of critical care medicine by allowing anyone anywhere to initiate life-saving procedures. Since its introduction, it has been taught worldwide and used innumerable times on victims of cardiac arrest. It is standard procedure worldwide in treating victims of heart arrest, asphyxiation or other lethal emergencies.

There are, however, limits to the application of standard CPCR because sternal compression cannot reliably produce enough blood flow to maintain viability of vital organs. Moreover, prolonged life support (PLS) after restoration of a heartbeat has its limits without the availability of artificial circulation and oxygenation.

This need led to the development of emergency cardiopulmonary bypass (CPB). CPB permits the control of flow, pressure, temperature and oxygenation of the blood. See Safar et al., "Cardiopulmonary Bypass for Emergency Resuscitation after Prolonged Cardiac Arrest", *American Journal Of Emergency Medicine*, 2:348, 1984.

It is known that periods of no-blood flow to the brain can seriously effect brain function. Therefore, the key element in resuscitation is to start life-saving procedures as quickly as possible after onset of cardiac arrest. The known machines to accomplish CPB are not portable and are not easily used where a cardiac arrest or trauma victim is located. For example, U.S. Pat. No. 4,540,399 discloses a closed emergency heart bypass system for extracorporeal blood circulation. The system includes a pump and an oxygenator. There is no disclosure concerning using this device at the scene of an accident or a heart attack.

Another advantage of CPB over CPCR is that CPB can be used in association with other techniques to prevent or correct derangements encountered in terminal states and clinical death such as rapid blood loss, blood gas derangements, temperature extremes and intoxication. CPB can be used in association with methods to purify blood and to provide hemoadsorption, plasma and blood cell apheresis. Other procedures that can be used in association with CPB are heating or cooling the blood and total body blood wash-out and blood replacement. Therefore, any CPB apparatus should be adapted to accommodate modules to accomplish these procedures.

Therefore, there is a need for a CPB apparatus that is portable and easily transported to an accident scene or heart attack victim. The apparatus should be adapted to include one or more means for conditioning the blood of the patient while performing CPB.

SUMMARY OF THE INVENTION

The portable and modular cardiopulmonary bypass apparatus has met the above mentioned needs. The apparatus consists of (i) a first cannula assembly means for withdrawing blood from a patient, (ii) a pump means connected to the first cannula assembly means for receiving the withdrawn blood and for moving the blood through the apparatus, and (iii) a first tubing means connected to the pump means to transport the patient's blood away from the pump means. The apparatus further comprises (iv) oxygenator means for receiving blood from the first tubing means and for oxygenating the blood and (v) second cannula assembly means connected to the oxygenator means for returning the oxygenated blood to the patient. The apparatus is portable so that it can be used by medical personnel anywhere. In addition, the apparatus is adapted to include one or more modules for conditioning the blood, such as modules that include a heat exchanger, blood purifier, plasma and blood cell apheresis device and others. An aortic balloon catheter is also provided.

It is an object of the invention to provide an apparatus for CPB which is portable such that it can be used at the scene of an accident or of a patient having cardiac arrest or other life threatening emergency.

It is a further object of the invention to provide an apparatus that provides life saving CPB at the earliest possible time either inside or outside a hospital.

It is a further object of the invention to provide a portable CPB apparatus that can be adapted to contain several blood conditioning modules.

It is a further object of the invention to provide an aortic balloon catheter module associated with the CPB apparatus to provide differential perfusion of selective regions of a patient's body.

It is a further object of the invention to provide a massive blood infusor module to supplement or replace a patient's blood.

It is a further object of the invention to provide a blood heat exchanger to control the temperature of a patient's blood.

These and other objects of the invention will be more fully understood from the following description of the invention with reference to the drawings appended to this application.

DESCRIPTION OF THE PREFERRED EMBODIMENT

AS used herein, the term "portable" is defined as being able to be transported with relative ease by one adult of normal strength and size. Also, as used herein, the term "patient" refers to any member of the animal kingdom, including but not limited to human beings.

Figure 1:
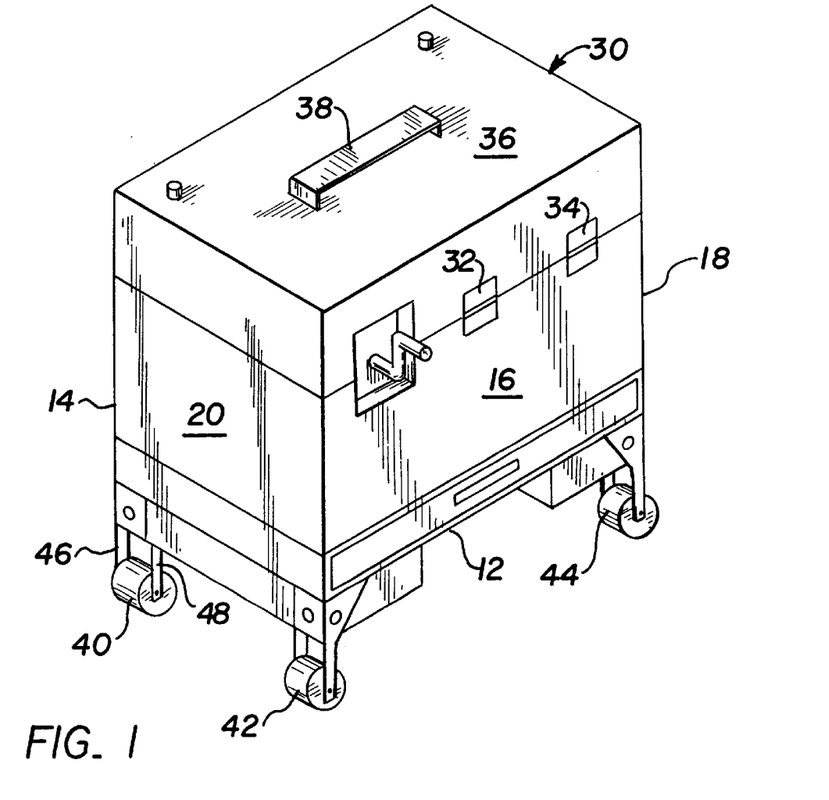
FIG. 1 is a perspective view of the apparatus in a closed position ready for transport to (i) the scene of an accident or (ii) a victim of heart arrest or other lethal emergency.
Figure 1A:
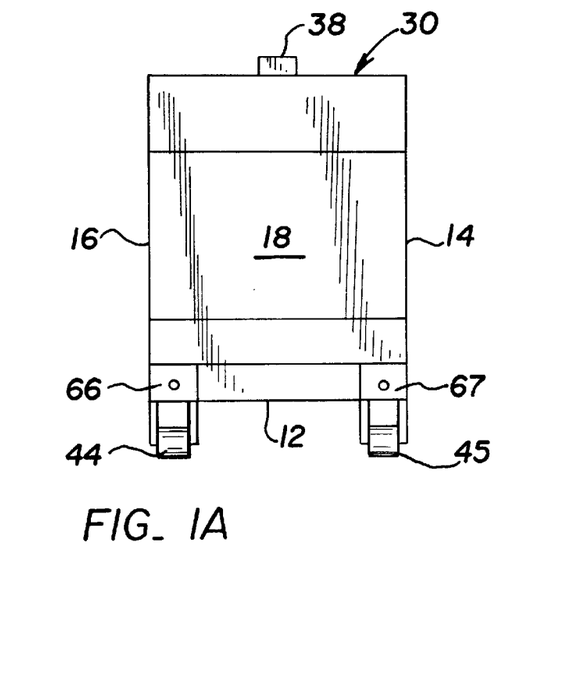
FIG. 1A is a rear elevational view of the apparatus in a closed position.

Referring to FIGS. 1 and 1A, the apparatus of the invention is shown. The apparatus consists of a base 12, a first sidewall 14, a second sidewall 16, a back wall 18 and a front wall 20. The apparatus further consists of a lid 30 which is connected by a hinge (not shown) to sidewall 14 and which is further connected to the second sidewall 16 by two locking means 32 and 34. The top wall 36 of the lid 30 is equipped with a carrying handle 38 to facilitate transporting the apparatus.

Connected to the underside of the base 12 are four wheels 40, 42, 44 and 45. The wheels are mounted on axles (not shown) that are connected to a pair of axle supports such as for example 46 and 48 of wheel 40. If desired, locking means can be provided on the wheels. The opposite ends of the axle supports 46 and 48 are attached to the base 12 as by welding or the like.

The apparatus is preferably fifteen (15") inches in height, twenty (20") inches in length and twelve (12") inches in width. The unit is preferably less than fifty (50) pounds in weight and is made of shock-resistant light weight materials such as vacuum foamed plastic. It will be appreciated that the dimensions, weight and materials used are presented as examples only and the invention is not limited thereby, except that the apparatus should be portable as defined hereinabove.

Figure 2:
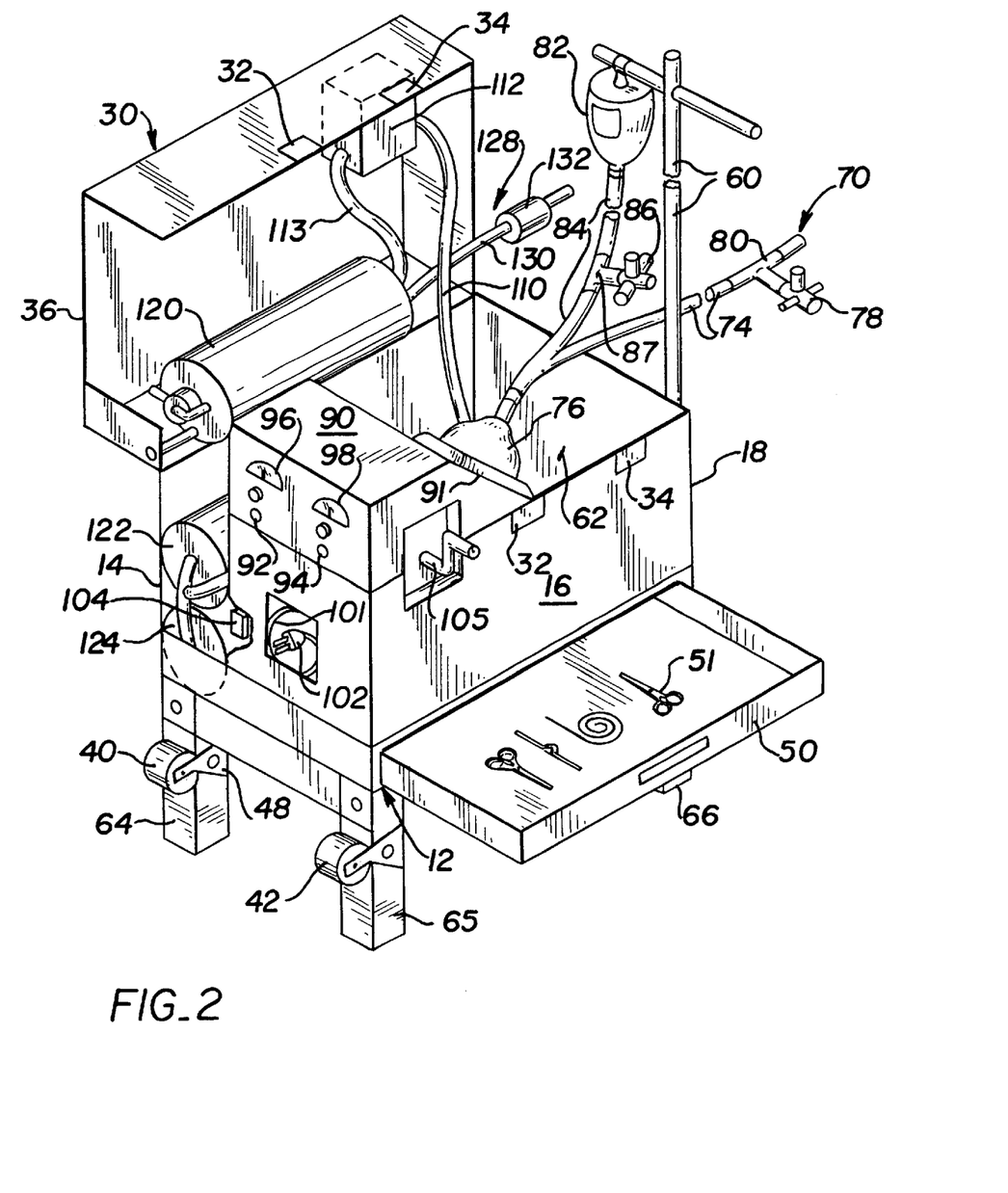
FIG. 2 is a perspective view of the apparatus in an open position such that it is ready to be used on a trauma or heart attack victim.

Referring now to FIG. 2, the apparatus is shown with the lid 30 opened and front wall 20 removed thus exposing the various devices used for life-saving CPB. The lid 30 can be optionally provided to be rotated 180° to form a substantially horizontal surface that can serve as a tray or stand for other modules and/or provide extra space for placing other items such as intubation, surgical and drug administration supplies. A drawer 50 is also provided which is retractable from the base 12. The drawer 50 forms a surgical instrument tray when pulled away from the apparatus. The drawer 50 can contain items 51 required for vascular access. These items include vascular catheters and surgical instruments such as scalpels, scissors, clamps and sutures. The apparatus is also provided with a retractable I-V stand 60 which can be folded and stored in the cavity 62 of the apparatus formed by the base and sidewalls. Also stored in the cavity can be a spare CPB circuit and sterile plasma or blood substitute bags for primary and initial fluid resuscitation.

Once the apparatus is positioned for use, retractable legs 64, 65, 66 and 67 which are associated with each wheel 40, 42, 44 and 45 can be used. The retractable legs are pivotally mounted to the underside of the base 12 of the apparatus. The retractable legs not only provide stability for the apparatus when in use, they also provide extra height and tilt. The tilt is provided by making legs 64 and 65 shorter in height than legs 66 and 67.

The CPB apparatus further consists of a first cannula assembly means 70 which is designed to be placed in a patient's venous blood vessel for withdrawing venous blood therefrom. The first cannula assembly means 70 as shown is a venae cavae cannula which can be inserted via the femoral vein and is non-kinking, multihole, large bore, long, thin-walled and preferably heparin bonded. One example of a commercial cannula assembly means is a model made by Medtronics. The first cannula assembly means 70 has a stylette and is insertable either by cut down of, for example, the femoral vein or by a guidewire (Seldinger Technique) or both. The first cannula assembly means 70 includes a tube 74 which flows blood into the pump 76. A stopcock 78 and T-tube 80 are provided on the tube 74 for administration of drugs, sampling of venous blood or drawing of venous blood in the case of blood exchange. The I-V stand 60 can contain an I-V bag 82 which is connected to a tube 84 that is in turn connected to the first cannula assembly means 70. It will be appreciated that the I-V stand 60 can accommodate more than one I-V bag. Tube 84 as shown is also provided with a stopcock 86 and T-tube 87.

The pump 76 receives the withdrawn venous blood from the patient and transports this blood through the apparatus. The pump 76, as shown, is preferably a non-occlusive centrifugal pump such as Model No. BP80 made by Biomedicus Company of Eden Prairie, Minn., U.S.A. The pump 76 preferably can pump up to ten (10) liters per minute. The pump 76 is mounted on a pump console 90 by means of an interchangeable pump base 91 which will facilitate attachment of various pump heads. The pump console 90 contains controls 92 and 94 to control the rpm of the pump 76 and the flow rate of the fluid through the pump 76, respectively. The pump rpm is displayed on meter 96 and the pump flow rate is displayed on meter 98. In this way, the operator can control both of these functions of the pump 76.

The pump 76 is powered by either (i) an AC power source which is accessed by a cord 101 and AC plug 102; (ii) a battery gel-pak 104 which is mounted in the cavity 62 as is shown in the partially cut away view of FIG. 2; or (iii) a hand crank 105 which engages the pump shaft of pump 76 by means of a bendix gear (not shown). It will be appreciated that the AC power source as accessed by the cord 101 and plug 102 are preferred to be used, however, if there is no ready AC power source, the battery gel-pak 104 will provide the necessary power to run the apparatus. Finally, if an AC power source is not available and the battery gel-pak is inoperable, the hand crank 105 can be used.

Another tubing means 110 is connected to the outlet end of the pump 76. This tubing means 110 runs through an electromagnetic flowmeter 112 which is connected to the console and ultimately the flow rate control 94 and display 90. The electronic signals from the flowmeter 112 are transferred to the pump console 90, where they are converted to rpm and flow rate indications which are displayed on the rpm meter 96 and the flow rate meter 98.

Another tube 113 connects the electromagnetic flow meter 112 to the oxygenator 120. The oxygenator 120 is preferably a membrane oxygenator. The oxygenator 120 includes oxygen tanks 122 and 124 which are also stored in the apparatus. The tanks preferably hold one thousand (1000) liters of oxygen which will provide over two hours of operating capacity. Because of the tilt of the apparatus due to the retractable legs 64, 65, 66 and 67, the oxygenator 120 is obliquely positioned to make the bubbles created therein rise to the top to facilitate removal of the air ("debubbling") from the oxygenated patient blood.

A second cannula assembly means 128 as shown includes a tube 130 that receives the oxygenated blood from the oxygenator 120 and returns it to the patient's arterial system such as through the femoral artery. The second cannula assembly means 128 includes a blood filter and bubble trap 132 which filters bubbles and clots. The second cannula assembly means 128 can be a short twelve to eighteen trench size arterial cannula with multiple holes.

It will be appreciated that the entire circuit that is in contact with the blood, with perhaps the exception of the pump 76 head which receives high flows, is preferably heparin bonded. This will avoid systemic heparinazation of the patient, which as is known, can increase bleeding tendency in the patient. Heparin bonding is a patented procedure owned by Medtronics.

In use, the apparatus is carried by qualified medical personnel to a patient in need of CPB. The retractable legs can be set to position the apparatus. The lid locking means 32 and 34 are released and the lid 30 is opened. Patients in terminal state (severe shock or hypoxemia) or cardiac arrest who do not respond to standard resuscitative efforts over a reasonable period of time (usually minutes) would be approached by the CPB team. During ongoing standard resuscitation, femoral vessel access will be established, the venae cavae cannulated via the femoral vein and the femoral artery cannulated—both either by cutdown or the so-called "Seldinger Technique" with use of needle and guidewire. During the vessel access procedure, another person is priming the CPB circuit with plasma substitute. The apparatus, however, can be preprimed (as will be explained hereinafter with respect to FIG. 3). Initiation of CPB after vessel access is done as rapidly as possible. Pump flow is initiated with the highest rpm possible and then adjusted depending on whether there is no flow or low flow of spontaneous circulation. All treatment is "titrated" to the patient's monitored variables, which change rapidly during the reversal of terminal states or clinical death. Once spontaneous circulation is started with or without defibrillating countershocks and drug usage, the total bypass (controlled circulation) via oxygenator is transformed into a partial bypass and as soon as clinically feasible the patient is weaned from bypass.

As explained hereinbefore, the apparatus can be adapted to include one or more modules for conditioning the blood of the patient while performing CPB. The modules that can be adapted for use with the apparatus are (1) blood temperature controller, (2) blood volume infuser and exchanger, (3) blood purifying modules, (4) aortic balloon catheter and (5) arterial and venous oxygen monitors.

Figure 3:
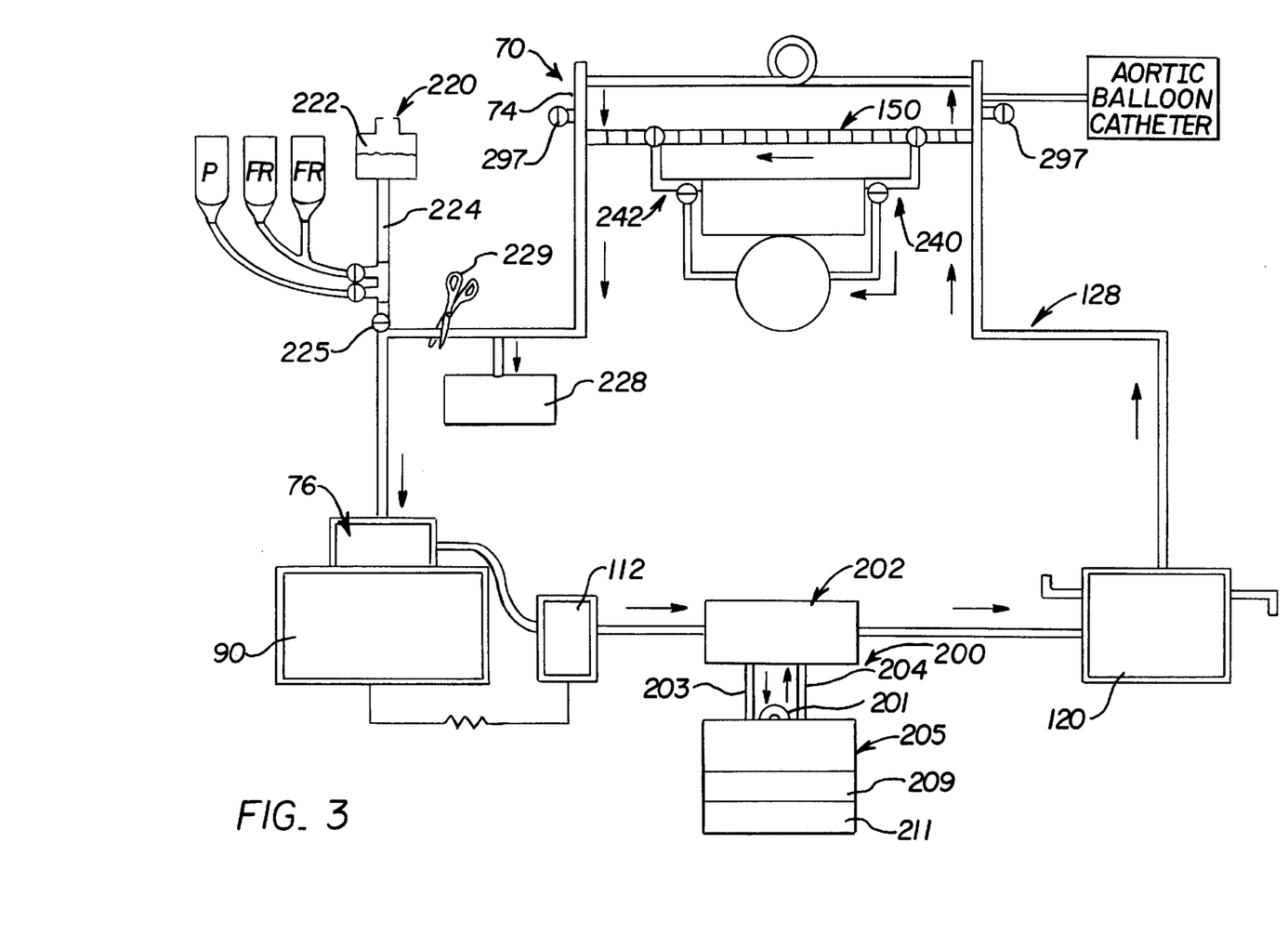
FIG. 3 is a schematic view of the "core unit" of the apparatus showing how and where the various modules are adapted to be attached thereto.

Referring to FIG. 3, a schematic diagram of the apparatus and the above five modules is shown. The core unit of the apparatus is shown. The core unit consists of the patient first cannula assembly means 70 including cannula tube 74, the pump 76, the pump console 90, the electromagnetic flowmeter 112, the membrane oxygenator 120 (which includes the oxygen tanks 122 and 124 not shown on FIG. 3) and the second cannula assembly means 128. The operation and use of the core unit of the apparatus was explained hereinabove with respect to FIGS. 1 and 2. The five modules discussed hereinabove are provided in separately portable units for use with the core unit of the apparatus. In this way, blood conditioning can take place at the same time as CPB.

Also illustrated in FIG. 3 is a shunt circuit 150. The shunt circuit permits recirculation of the priming fluid prior to opening up of circulation to the patient. The shunt circuit also permits control of priming fluids temperature (for example, for induction of hypothermia with CPB) during vessel access, so that the first fluid entering the patient is at the desired lower temperature. The opposite would hold for treating hypothermic arrest, so that the first fluid entering the patient is about five to ten degrees Centigrade (5°–10° C.) above body temperature to rewarm the patient.

The blood temperature controller module 200 is shown in FIG. 3. The blood temperature controller module 200 is provided in a separate case. The blood temperature controller module 200 consists of miniaturized fluid circuit with a pump 201 delivering temperature controlled warmed or cooled solution (usually water) through a blood heat exchanger 202. The pump 201 can preferably move up to ten (10) liters per minute through the exchanger 202. The solution is circulated through tubes 203 and 204 (in the direction of the arrows) into the controller unit 205 and the blood heat exchanger 202.

As is known, the warmed or cooled solution is passed through the heat exchanger 202 at the same time as the blood from the pump 76. The cooling is accomplished by immersion of the solution in ice, $CO_2$ ice, blue gel ice container, or other suitable source 209. The solution can be warmed by providing an electric immersion heater 211, for example. The solution and the blood do not contact each other but are separated by a membrane which allows the temperature of the solution to control the temperature of the blood. The solution is continually circulated through the controller unit 205 and the blood heat exchanger 202. The heat exchanger unit is capable to lower the venous inflow blood temperature by at least five degrees Centigrade (5° C.) through the heat exchanger at a flow rate of ten (10) liters per minute to permit rapid induction of mild, moderate or deep hypothermia for an adult. The pump 201 preferably can move up to ten (10) liters of fluid per minute through the exchanger. The module would also contain a battery, a thermometer to monitor the water temperature, temperature monitors for continuous display of the patient's nasopharyngeal or tympanic membrane temperature and esophageal temperature.

FIG. 3 shows the second module, a blood volume infusor and exchanger 220. This module 220 is used for delivery of large volumes of plasma substitute, blood substitute (e.g., stroma free hemoglobin) or whole blood, optionally with special agents such as preservation or resuscitation drug cocktails. The module 220 can be provided in a separate portable case. This module 220 will be connected to the venous side or first cannula means tube 74. The module 220 will include containers for blood, plasma substitutes and blood substitutes. The blood, plasma substitutes or blood substitutes will be placed in a reservoir 222 which is connected to the first cannula assembly means on the venous side of the apparatus. The reservoir 222 is preferably made of plastic and preferably of a ten (10) liter capacity. Tubing 224 is used to carry the blood, blood or plasma substitute from the reservoir 222 to the first cannula tubing means 74 by means of a Y-connector 225. Also provided are means for mixing into the infused blood other fluids such as fluid resuscitators "FR", or plasma or plasma substitutes "P" with or without drugs to be administered by infusion. The module 220 can also include kits for checking of hematocrit and activated clotting time. Finally, a ten (10) liter plastic drainage reservoir 228 is provided that can be connected at the patient side of the tubing 74 for collecting blood from the patient when a rapid blood exchange from the arterial side is to be accomplished. A clamp 229 can also be provided between the drainage reservoir 228 and the Y-connector 225.

This will be used in cases of severe rapid hemorrhage and in cases where the patient's own blood is to be replaced as in suspended animation with blood washout and deep cooling.

The third module is the blood purifying module 240. Once emergency resuscitation with circulation of adequate blood volume has been accomplished, one may want to detoxify the blood by one of several ways. This can be accomplished by attaching one of the commercially available blood purifying units (e.g., hemabsorption filter and apheresis apparatus) rapidly and easily to the core unit. The driving force is the core unit's blood pump. A sidearm 242 of the core unit's arterial line is connected in parallel with the priming shunt circuit 150, to the first cannula assembly means 70. One option is a continuous low flow side stream as, for example, through a charcoal hemabsorption filter. Another example is that of intermittent withdrawal of increments of the patient's arterial or venous blood for modification in a plasma or cell apheresis apparatus. The modified blood is returned by gravity into the first cannula assembly means 70.

The presently commercially available detoxifying devices that might be attached include those that could provide one of the following treatments: hemabsorption by means of a charcoal filter for example; hemofiltration (mostly for water removal); hemodialysis (artificial kidney); plasma and blood cell apheresis (e.g., Hemonetics plasmapheresis unit); and extracorporeal heating or ultra-sound or other novel treatment of blood for killing bacteria or viruses. Removal of "sick" white blood cells is becoming a novel experimental therapy for multiple organ failure, including the postresuscitation syndrome. Exchange of the patient's "sick" plasma for fresh plasma or plasma substitutes, has been effective in some chronic conditions such as paralyzing polyneuritis and myasthenia gravis, for which the treatment with such a portable and miniaturized unit would become more readily available.

The fourth module is the aortic balloon catheter shown only schematically in FIG. 3. This catheter is used (i) to stop lethal hemorrhage below the chest (ii) to permit experimental differential perfusion, cooling or warming of heart, brain or viscera and (iii) for extracorporeal membrane oxygenation in lung failure with spontaneous circulation. The catheter can be used independently of the CPB circuit to deliver medications or other fluids to the patient or can be used to take the place of the second cannula assembly means 128 to permit differential perfusion of various regions of the body, as will be explained herein-after.

Figures 4, 5:
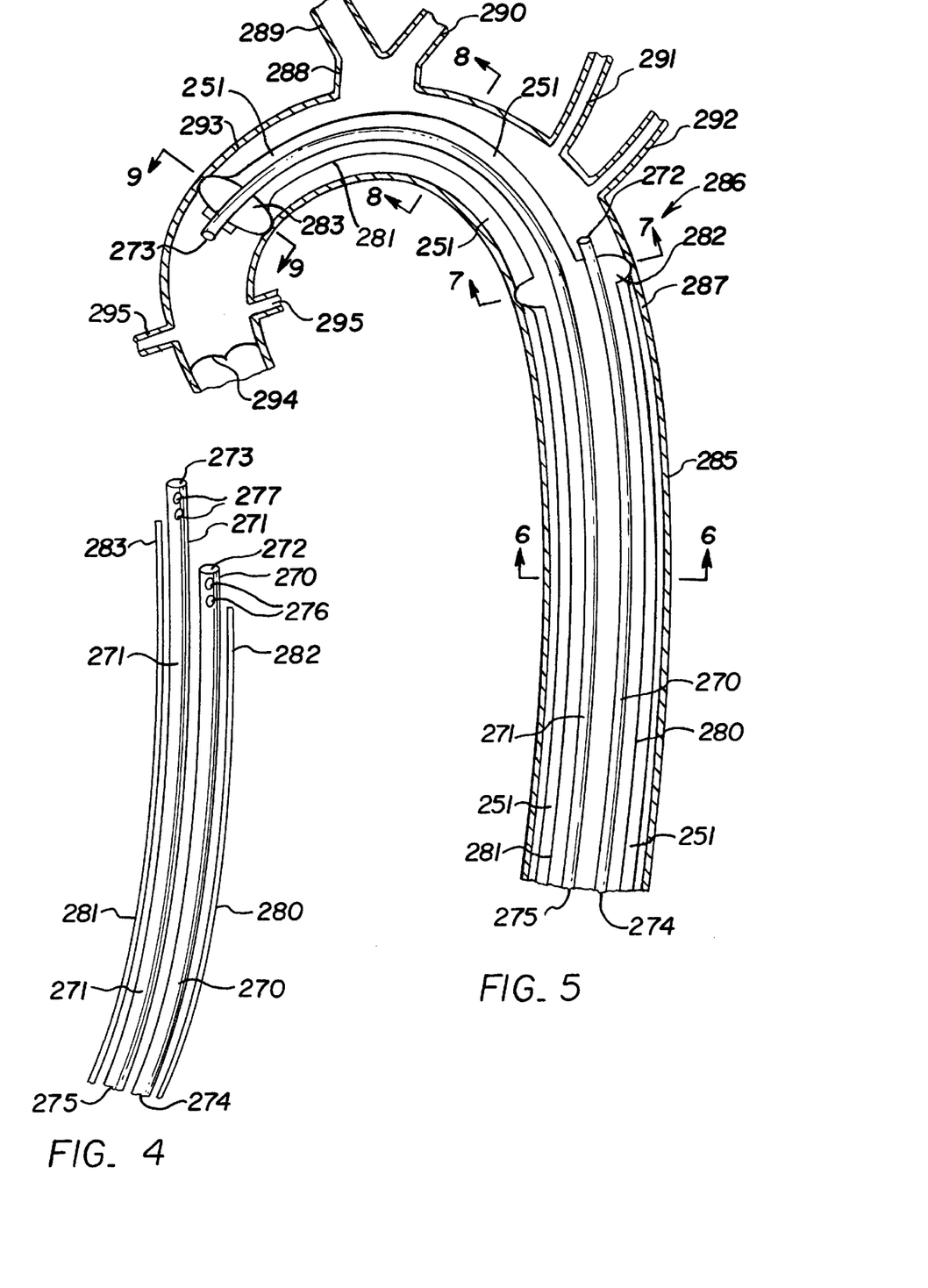
FIG. 4 is a perspective view of the aortic balloon catheter of the invention with its outer covering removed for clarity of explanation.
FIG. 5 is a cross-sectional view of the catheter of the invention as it is in position in the aorta of a human.

Referring to FIGS. 4 and 5, the aortic balloon catheter of the invention is shown. The outer tube 251 in which the catheter is positioned is not shown in FIG. 4 for clarity of illustration, but a cross-sectional view of the outer tube 251 is shown in FIG. 5. The catheter is about sixty centimeters long (for adult use) having a diameter of about 18–22 French OD. The catheter is preferably thin walled and non-kinking. The catheter has a first lumen 270 and a second lumen 271. Lumen 270 has an open internal end 272 and an external end 274. The external end 274 of lumen 270 forms part of the cannula assembly means (not shown) that is used to connect the CPB machine or a drug or liquid source to the catheter. Lumen 271 also has an open internal end 273 and an external end 275. External end 275 also forms part of the cannula assembly means (not shown) that is used to connect the CPB machine or a drug or liquid source to the catheter. It will be appreciated that multiple holes 276 and 277 can be provided in the first and second lumens near the respective open internal ends 272 and 273.

The catheter also includes first pilot tubing 280 and second pilot tubing 281. First pilot tubing 280 has an end that communicates with the interior of a first balloon 282. Second pilot tubing 281 has an end that communicates with the interior of a second balloon 283. FIG. 4 shows balloons 282 and 283 being deflated. FIG. 5 shows the balloons 282 and 283 as inflated. In order to inflate the balloons 282 and 283, pump means (not shown) which communicates with the ends of the pilot tubing 280 and 281 provides a fluid, such as air, which is delivered to the balloons 282 and 283 via the respective first and second pilot tubing means 280 and 281. The pump means can include valves, regulators and gauges as is well known to those skilled in the art. The pump means can independently control the inflation or deflation of the first and second balloons so as to allow selective inflation or deflation thereof.

As can be seen in FIGS. 4 and 5, balloon 282 is positioned below the internal open end 272 of lumen 270 and the second balloon 283 is positioned below the open internal end 273 of lumen 271 but above the open internal end 272 of lumen 270.

Referring now more particularly to FIGS. 5–9, the catheter in its outer covering 251 is shown as positioned in the aorta 285 of a human adult 286. The outer covering 251 surrounds the lumens 270 and 271 and pilot tubing 280 and 281 and is made of any suitable material known to those skilled in the art such as any resinous material. As was explained hereinbefore, the catheter can be used in place of the second cannula assembly means 128 in order to complete the CPB circuit to deliver oxygenated blood from the CPB apparatus (FIGS. 1–3). The catheter can also be used independently of the CPS apparatus to deliver drugs or other fluids from a source (not shown) to the patient. It will be appreciated that the catheter is inserted into the femoral artery (not shown), similarly to the way that the second cannula assembly means 128 is inserted into the patient.

FIG. 5 shows both first balloon 282 and second balloon 283 being inflated. The first balloon 282 is positioned in the descending aorta 287 below the brachiocephalic trunk 288 (which forms the right subclavian artery 289 and the right common carotid artery 290) as well as below the left common carotid artery 291 and the left subclavian artery 292. The second balloon 283 is positioned in the ascending aorta 293 and just above the aortic valve 294 and the coronary arteries 295.

Figure 6:
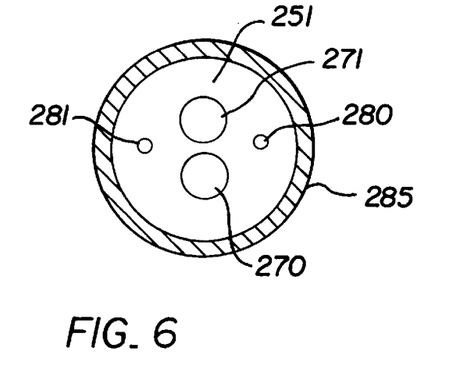
FIG. 6 is a cross-sectional view taken along line 6—6 of FIG. 5.
Figure 7:
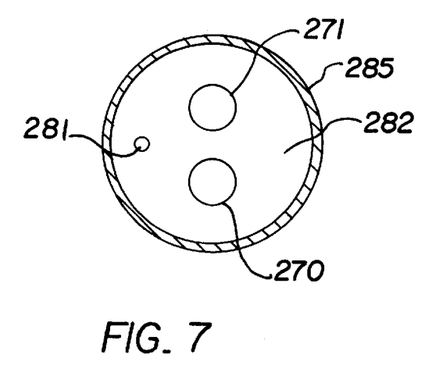
FIG. 7 is a cross-sectional view taken along line 7—7 of FIG. 5.
Figure 8:
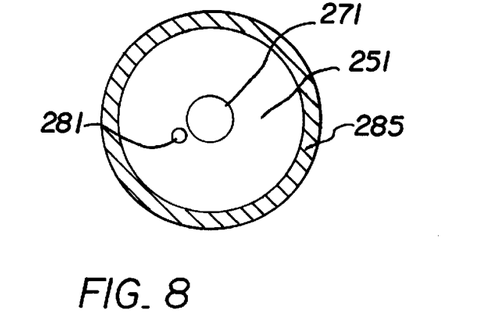
FIG. 8 is a cross-sectional view taken along line 8—8 of FIG. 5.
Figure 9:
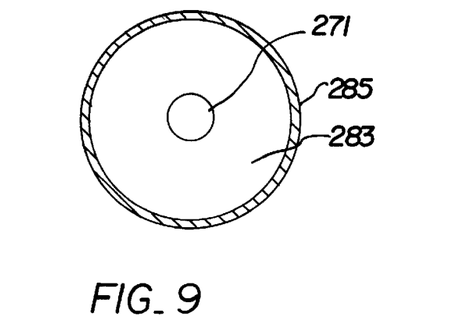
FIG. 9 is a cross-sectional view taken along line 9—9 of FIG. 5.

Referring more particularly to FIG. 6, it will be seen that the catheter contains lumens 270 and 271 as well as pilot tubing 280 and 281. The lumens 270 and 271 and pilot tubing 280 and 281 are placed in the catheter outer covering 251. The catheter is positioned in the aorta 285 of the patient 286. When balloon 282 is inflated (FIG. 7), it sealingly engages the interior wall of aorta 285 to block the aorta 285. Lumens 270 and 271 as well as a pilot tubing 281 continue to extend beyond balloon 282. In this way, fluid can flow through lumens 270 and 271 past balloon 282. Lumen 270 open internal end 272 is positioned in between balloons 282 and 283, so only lumen 271 and 281 remain in the catheter as shown in FIG. 8. The catheter 250 has a reduced diameter at this point. Finally, when balloon 283 is inflated (FIG. 9), it also blocks aorta 285. Fluid from lumen 271 can flow therethrough past balloon 283 and out open end 273.

It will be appreciated that differential perfusion to the head and/or heart can be accomplished by using catheters. If neither balloon 282 and 283 is inflated, a preferential supply of blood and/or medications can be supplied to the arteries leading to the head, i.e., the right subclavian 289, right carotid 290, left subclavian 291 and left carotid 292 (hereinafter referred to as "head arteries") and the coronary arteries 295 (hererinafter referred to as "heart arteries") but the blood and/or drugs will also be circulated to the rest of the body.

If only first balloon 282 is inflated, a supply of blood or drugs will be delivered to the head arteries and the heart arteries to selectively perfuse the head and heart as well as providing hemostasis in severe hemorrhage below the thorax, as for example, the result of severe trauma or rupture of the abdominal aorta. If the catheter is used in place of the second cannula assembly means 128 when performing CPB as by using the CPB apparatus of the invention, it will be appreciated that the venous blood withdrawn from the venae cavae of the patient will be oxygenated and returned directly to the head and heart arteries, with no blood being lost because of trauma below the thorax. The oxygenated blood will be delivered to the heart and head and will return to the venae cavae via the venous system. At this point the cycle begins again with the venous blood being withdrawn from the patient's venae cavae by the first cannula assembly means 70 into the CPB apparatus for oxygenation.

If only second balloon 283 is inflated, a supply of blood or drugs is delivered only to the heart arteries. Blood can be circulated only to the heart arteries in the case of head and/or lower extremity trauma.

If both balloons 282 and 283 are inflated, arterial perfusion and/or delivery of medication can be achieved in three different compartments. The head can be perfused through lumen 270, the heart can be perfused through lumen 271 and the rest of the body can be perfused by use of the second cannula assembly means 128 of the CPB apparatus.

It will be appreciated that these manipulations allow control of the composition and temperature of perfusion fluid (blood or medications) to the heart, to the head and to the rest of the body independently. These manipulations and combinations permit stopping bleeding in the head or the rest of the body in case of trauma by selectively not perfusing that particular region of the body.

For differential perfusion, cooling, warming, or special fluid or drug administration to heart and/or brain and/or viscera, the catheter is inserted fully, with its tip placed just above the aortic valve 294, and the second balloon 283 inflated in the ascending aorta 293. The ascending aorta is eight to ten centimeters (8–10 cm) long in adult humans. This insertion ideally should be by emergency fluoroscopy, but might be possible by external measurements and the markings on the catheter without fluoroscopy, or under incision with the chest open.

For suspended animation, to enable resuscitative surgery in "irreparable" injuries, one might start cooling the whole organism moderately via the standard CPB circuit. When spontaneous heartbeat has ceased, the catheter is inserted in order to deliver different temperatures and solutions to heart, brain, and viscera. One can then at the end of a deliberate arrest of one to two hours resuscitate, for example, the heart before the brain.

For lung failure with spontaneous circulation (spontaneous heartbeat), both balloons remain deflated. The catheter is inserted into the ascending aorta as an alternative to a regular nonballoon catheter of the same length. The catheter tip is placed into the ascending aorta 293 in order to deliver variable low flow rates of oxygenated blood, which in addition to the cardiac output from the left ventricle, achieves better oxygenation for heart and brain. A peripheral catheter would achieve this only for the lower part of the body.

In all usages of this device, the aortic balloon catheter would be used interchangeably or simultaneously with the standard short femoral artery cannula CPB circuit on the opposite side, from the apparatus (FIG. 3).

Insertion of the catheter through the femoral artery is preferred since the other option (its insertion through the axillary or neck) would encroach on the lumen of the cerebral blood flow.

For differential perfusion cooling and warming of the heart, brain, or viscera, there are now explorations ongoing concerning the relative tolerance of therapeutic deep hypothermia levels by heart and/or brain and/or viscera. There is a suggestion that temperatures near freezing are well tolerated by the brain, which would protect it against lack of oxygen during deliberate circulatory arrest to facilitate surgery, while the same very low temperatures cannot be tolerated by the heart without hurting it permanently. Also, the drugs most effective for brain resuscitation may differ from these most effective for heart resuscitation.

For use with the heart beating and lung failure, early use in lung failure of low flow delivery of oxygenated blood into the ascending aorta might make potentially injurious artificial ventilation unnecessary. Japanese investigators have called this treatment "extracorporeal lung assist" (ECLA). They used regular single lumen catheters for veno-arterial or veno-venous oxygen enrichment. This idea was preceded by the use of somewhat higher flow delivery of oxygenated blood into the ascending aorta in patients already with advanced pulmonary consolidation, in whom standard ventilator care cannot maintain blood oxygenation. This has been called "extracorporeal membrane oxygenation" (ECMO). In the multipurpose use of the invention, with balloons deflated, merely a catheter delivering a modest adjustable flow of oxygenated blood added to spontaneous cardiac output, often needed for many days, might sometimes "turn the tide" in progressive lung failure like "shock lung" or severe pneumonia.

Referring back to FIG. 3, the fifth module is a temperature sampling port 297. This optional adjunctive module is near the sampling ports of the core unit's first cannula assembly means 70 and second cannula assembly means 128. Both would either contain an electrode for oxygen tension monitoring, or an oximeter as now used percutaneously or invasively in critical care. The arterio-venous oxygen value differences and their relative changes will be used to guide the needed flow rates to be set on the electrical console of the core unit, to provide sufficient arterial oxygen transport for the organism's overall oxygen uptake.

It will be appreciated that a portable and modular cardiopulmonary bypass apparatus (CPB) has been provided. The CPB apparatus is portable so that it can be used at the scene of an accident or at the scene of a patient in cardiac arrest. The CPB can be used with several different modules for conditioning the blood, such as modules that include a heat exchanger, blood purifier, plasma blood cell apheresis and temperature monitor and with an aortic balloon catheter. The aortic balloon catheter is used to stop lethal hemorrhage below the chest, to permit experimental differential perfusion and for extracorporeal membrane oxygenation in lung failure with spontaneous circulation.

Whereas a particular embodiment of the invention has been described above, for purposes of illustration, it will be evident to those skilled in the art that numerous variations of the details may be made without departing from the invention as defined in the appended claims.

What is claimed is:

1. A portable and modular cardiopulmonary bypass apparatus comprising:

first cannula assembly means for withdrawing venous blood from a patient;

pump means connected to said first cannula assembly for receiving said withdrawn venous blood and for moving said blood through said apparatus;

first tubing means connected to said pump means to transport said blood away from said pump means;

oxygenator means for receiving said blood from first tubing means and for oxygenating said blood;

second cannula assembly means connected to said oxygenator means for returning said oxygenated blood to said patient's arterial system;

temperature module means for effecting blood temperature control; and said apparatus being portable.

2. The apparatus of claim 1, wherein said apparatus includes blood temperature control module means having a heat exchanger which warms or cools said patient's blood, a controller unit having a pump which pumps warm or cool fluid into said heat exchanger and circulation tubes connecting said heat exchanger to said controller unit.

3. The apparatus of claim 1, wherein said apparatus includes blood or blood substitute infusing and exchange module means having a fluid reservoir means for holding fluid to be infused into said first tubing means.

4. The apparatus of claim 3, including means for introducing into said infused blood other agents.

5. The apparatus of claim 1, wherein said apparatus includes blood purifying module means having means for performing at least one of the following: (i) hemoabsorption; (ii) hemofiltration; (iii) hemodialysis; (iv) plasma and blood cell apheresis; (v) extracorporeal heating; and (vi) extracorporeal ultrasound.

6. The apparatus of claim 1, wherein said apparatus includes blood temperature sampling module means being at least one temperature sampling port electrode.

7. A portable and modular cardiopulmonary bypass apparatus comprising:

first cannula assembly means for withdrawing venous blood from a patient;

pump means connected to said first cannula assembly for receiving said withdrawn venous blood and for moving said blood through said apparatus;

first tubing means connected to said pump means to transport said blood away from said pump means;

oxygenator means for receiving said blood from first tubing means and for oxygenating said blood;

second cannula assembly means connected to said oxygenator means for returning said oxygenated blood to said patient's arterial system;

temperature module means for effecting blood temperature control;

said apparatus being portable; and surgical tray means removably stored in said apparatus.

8. The apparatus of claim 7, including retractable legs positioned on the underside of said apparatus, whereby said legs may be deployed when said apparatus is in use to stabilize said apparatus.

\* \* \* \* \*